United States Patent
Tate

Patent Number: 5,996,116
Date of Patent: Dec. 7, 1999

[54] BALL MARKER RETENTION SYSTEM

[76] Inventor: John R. Tate, 11621 Markon Dr., Garden Grove, Calif. 92841

[21] Appl. No.: 09/187,684

[22] Filed: Nov. 5, 1998

[51] Int. Cl.[6] .......................................................... A42B 1/24
[52] U.S. Cl. .................................. 2/12; 2/195.1; 2/200.1; 2/209.13; 2/425; 224/918
[58] Field of Search ........................... 2/12, 209.13, 422, 2/425, 195.1, 200.1; 224/918

[56] References Cited

U.S. PATENT DOCUMENTS

| | | | |
|---|---|---|---|
| 459,942 | 9/1891 | Brown | 2/209.13 |
| 4,627,621 | 12/1986 | Tate . | |
| 4,885,195 | 12/1989 | Change, III | 428/36.1 |
| 5,295,683 | 3/1994 | Tate . | |
| 5,305,999 | 4/1994 | Tate . | |
| 5,715,539 | 2/1998 | Benecki et al. | 2/160 |
| 5,898,943 | 5/1999 | Kim | 2/161.2 |
| 5,898,946 | 5/1999 | Keating et al. | 2/209.13 |

*Primary Examiner*—Diana Oleska
*Attorney, Agent, or Firm*—Charles H. Thomas

[57] ABSTRACT

A golf ball marker is carried in open display on a fabric article of golf clothing or other fabric golf accessory and remains in position due to the force of magnetism. To produce this effect, a layer of magnetic material is secured in position in contact with a concealed side of a layer of fabric in the article of golf clothing or other golf accessory. The golf ball marker is constructed of a ferrous material so that when it is placed into contact with an exposed surface of the same layer of fabric against which the magnetic material is secured opposite the layer of magnetic material, the ball marker is held by the force of magnetic attraction against the exposed surface of the to fabric layer. The ball marker remains in position until purposefully dislodged by a force that opposes the magnetic field created by the magnetic material. This force may be applied by the thumb and forefinger of the golfer's hand to remove the golf ball marker from the fabric layer. The layer of magnetic material may be incorporated into the bill or band of a hat or cap, the bill or band of a golf sun visor, the closure flap of a golfing glove, or in a golf towel.

10 Claims, 5 Drawing Sheets

BALL MARKER RETENTION SYSTEM

BACKGROUND OF THE INVENTION

1. Field of the Invention

The present invention relates to a system for releasably securing a golf ball marker to a fabric golf accessory, such as a golf hat, a sun visor, a golfing glove, or a towel, and an improvement to a fabric golf accessory by the combination of a magnetic material therewith.

2. Description of the Prior Art

Golf ball markers have been used for many, many years in order to mark the position of a golf ball on a fairway or green during a game of golf engaged in by competitive players. Golf ball markers are typically formed as small, disc-shaped structures, usually fabricated from metal. Conventional golf ball markers are often stamped from a ferrous material, usually steel or iron. Some conventional golf ball markers have a plain, unadorned appearance, although in more competitive golfing circles ball markers having surface embellishments on their faces are now widely utilized. Conventional ball markers may include the sculptured and/or painted reproductions of a golf course or tournament logo, a country club insignia, a corporate or university logo or insignia, or more personalized surface embellishments. Whatever the particular adornment adopted for a golf ball marker by a player, more often than not the player is proud to display the ball marker, since it is frequently indicative of courses or tournaments in which the player has participated or otherwise attests to the players experience or competence in participation in the game of golf.

While a player may be happy to display a ball marker, in conventional use, golf ball markers offer only a limited opportunity for such display. More often, when a golfer's ball lies in the field of play, the ball marker is typically carried in the golfer's pocket, and is thus concealed from view. Furthermore, when a golf ball marker is carried in a player's pocket, the player is often forced to dig and fumble through the contents of the pocket in order to retrieve it. Golf ball markers have similar sizes and shapes to coins of currency, which are often carried in the same pocket. A golf ball marker therefore cannot be separated easily from the other contents of the pocket by the sense of touch. The retrieval of a golf ball marker for use thereby creates a source of annoyance and distraction to the golfer.

Systems for enhancing the convenience of access and extent of display of golf ball markers have been devised in the past. For example, golf ball markers may be releasably mounted by means of magnets in golf divot tools that are utilized to repair divots and spruce up golf greens. Golf divot tools may be formed with one or more shallow, disc-shaped recesses therein at the bottom of which a flat slab of magnetic material is permanently secured. A ferrous ball marker formed of steel or soft iron may then be releasably held in position in the recess or tray of a golf divot tool by the magnetic force of attraction of the magnetic material. As a consequence, when the divot repair tool is utilized the ball marker is conveniently accessible and is also displayed for all to see. U.S. Pat. Nos. 5,295,683 and 5,305,999 disclose and describe divot tools of different configurations in which golf ball markers are releasably mounted by the force of magnetic attraction. Also, the tool of U.S. Pat. No. 5,305,999 includes a clip that may be attached to the belt, cap, shoe, pocket, or golf bag of a golfer. As a consequence, when the divot tool is carried in this manner the golf marker is more easily retrieved and is also prominently displayed. Nevertheless, since divot tools themselves are used only on limited occasions, the opportunities for conveniently retrieving a golf ball marker by releasably mounting it on a divot tool are somewhat limited.

SUMMARY OF THE INVENTION

The present invention involves a system in which a golf ball marker is retained in a very convenient and accessible location and prominently displayed throughout a game of golf. The ball marker retention system of the invention involves releasably positioning a golf ball marker on the exposed fabric surface of a golf accessory, such as an article of golf clothing. For example, golf ball markers may be prominently displayed on golf hats, caps, sun visors, golfing gloves, golf towels, golf bags, and other golfing accessories that are formed of fabric. The system for retaining golf ball markers in position in this manner involves the incorporation of a flat strip or slab of magnetic material or a plurality of flat magnetic discs or magnetic material in other shapes into the fabric structure of an article of golf clothing or some other golf accessory.

According to the invention, a slab, strip, or spot of magnetic material is mounted beneath the exposed surface of the fabric of an article of golf wear or a golfing accessory and secured out of sight. Nevertheless, the force of magnetic attraction acts through the fabric material with sufficient strength so that a ferrous golf ball marker will be held in position against the exposed surface of the fabric while the magnetic material exerting the magnetic field remains concealed from view on the inside, hidden surface of the fabric.

By utilizing the system of the invention, golf ball markers will adhere to articles of clothing and can be held in place by the force of magnetic attraction with a sufficient strength so that they will not become dislodged therefrom accidentally. To the contrary, the magnetic field exerted by the magnet through the cloth structure is sufficient to hold a ferrous ball marker firmly in position until and unless the user purposefully overcomes that force and pulls the ferrous ball marker clear of the magnetic field of attraction.

In one broad aspect the invention may be considered to be an improvement to a fabric golf accessory comprising: a layer of magnetic material embedded in the accessory, whereby the magnetic force of attraction of the magnetic material acts through the fabric structure of the accessory. The golf accessory may be a hat, a sun visor, a golfing glove, a golf towel, a golf bag, or any other article formed wholly or partially of fabric and utilized by a golfer while on a golf course.

The term fabric, as used herein, is to be construed in its broadest sense of any thin, expansive, flexible, or supple material of the type typically utilized in the construction of golf clothing and other golfing accessories. The term fabric should be construed as encompassing not only woven cloth textiles, but also other flexible, thin, expansive materials such as leather, plastic sheet material, and felt, for example.

In one preferred embodiment of the invention, the fabric golf accessory is a hat that has a bill formed of a stiff, substantially flat interior core. The core of the bill is encapsulated within a cloth fabric covering. The magnetic material may be glued or sewn into position atop the stiff, interior core forming the bill of the cap, and covered by the cloth fabric forming the cap.

The magnetic material may be a flexible sheet or layer of rubber with magnetized ferrous particles of iron or iron oxide embedded therein. Alternatively, the magnetic material may be comprised of a series of separate, thin, magnetic slabs, formed as discs, rectangles, or any other geometric shape. In still another alternative arrangement the magnetic material may be formed as lengths of magnetic wire. Magnetic material having other physical shapes may also be utilized.

In another broad aspect the invention may be considered to be in combination, an article of golf clothing formed of a flexible material having an exterior surface, a magnetic material permanently attached to the article of clothing beneath the exterior surface thereof, whereby the magnetic material exerts a magnetic field of attraction that acts through the flexible material, and a golf ball marker formed of a ferrous material placed in contact with the exterior surface of the flexible material within the magnetic field. The golf ball marker thereby adheres to the article of clothing on the exterior surface thereof unless dislodged therefrom by a force stronger than the magnetic field. The article of golf clothing may be a hat, sun visor, a golfing glove, or any other article of clothing, such as a shirt, jacket or pair of trousers.

In still another broad aspect the invention may be considered to be, in combination, a golf accessory constructed of fabric, a magnetic material permanently secured within the confines of the fabric so as to exert a force of magnetic attraction therethrough, and a golf ball marker formed of ferrous material located on the exterior of the fabric within the field of the force of magnetic attraction. The ball marker remains secured in place on the exterior of the fabric until removed by a force that overcomes the force of magnetic attraction.

In still another broad aspect, the invention may be considered to be a method of carrying a golf ball marker in open display on a fabric golf accessory comprising: securing a layer of magnetic material to a concealed surface of a layer of fabric of said golf accessory, and placing a golf ball marker formed of a ferrous material in contact with an exposed surface of said layer of fabric opposite the layer of magnetic material. The magnetic field produced by the layer of magnetic material acts through the layer of fabric to hold the golf ball marker against the exposed surface of the layer of fabric until an opposing force stronger than the magnetic field dislodges the golf ball marker from the layer of fabric.

The invention may be described with greater clarity and particularity by reference to the accompanying drawings.

DESCRIPTION OF THE EMBODIMENTS

Figure 1:
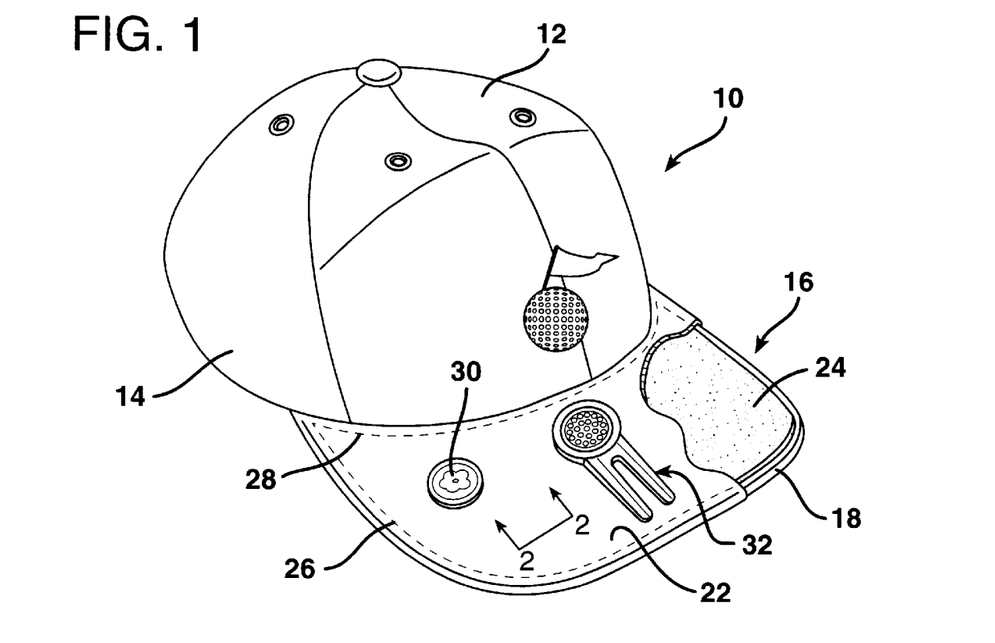
FIG. 1 is a perspective view of a fabric golf cap or hat in which a sheet of magnetic material is secured atop the core of the cap bill.

FIG. 1 illustrates a fabric-covered golf hat or cap indicated generally at 10. The cap 10 is formed with a cotton, wool, or synthetic fabric crown 12 surrounded by a hat band 14 at its lower extremity. In the forehead region a bill 16 is secured to the hat band 14. The bill 16 is constructed with a generally flat core 18, visible in the detail view of FIG. 2, which may be formed of fiberboard or some other material stiff enough to provide the bill 16 with a permanent shape. The flat, roughly crescent-shaped core 18 is wrapped within a sheet of fabric that forms a layer 20 on the underside of the bill 16 and an overlying fabric layer 22 that forms the upper, exposed surface of the bill 16.

Figure 2:
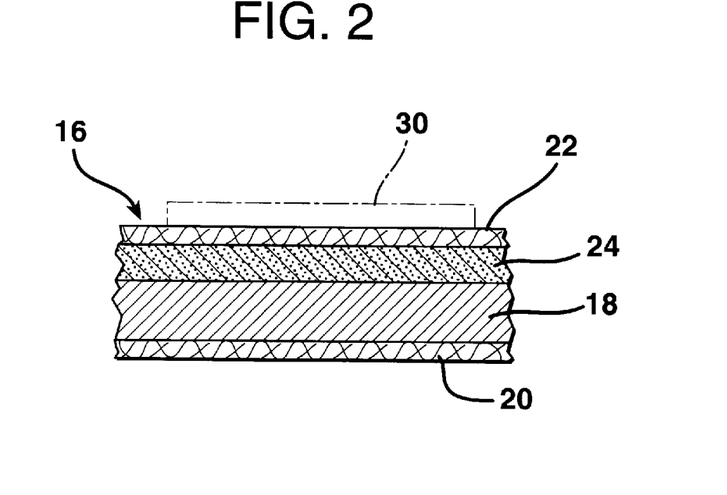
FIG. 2 is a sectional elevational detail taken along the lines 2—2 of FIG. 1.

A sheet 24 of rubber impregnated with magnetized ferrous particles of iron or iron oxide throughout is provided. The generally crescent-shaped sheet or slab of magnetic material 24 is cut only slightly smaller than the underlying stiffening core 18 of the visor bill 16. The sheet of fabric is wrapped over both the magnetic sheet 24 and the stiffening core 18 atop which the magnetic sheet 24 is placed. The magnetic sheet 24 is permanently secured in position atop the core 18 of the bill 16 by lines of stitching 26 and 28 that respectively define the periphery of the bill 16 and the junction between the bill 16 and the hat band 14 at the base of the crown 12. The lines of jo stitching 26 and 28 thereby hold the sheet of magnetic material 24 in a snugly confined manner entrapped between the core 18 of the bill 16 and the overlying fabric layer 22.

The fabric layer 22 is only fraction of an inch in thickness so that its presence does not materially attenuate the force of magnetic attraction exerted by the sheet of magnetic material 24 at the exposed upper surface of the fabric layer 22. As a consequence, a significant magnetic force is exerted through both the fabric layers 20 and 22 and is particularly strong atop the fabric layer 22 which lies in direct contact with the magnetic material 24.

As illustrated in FIG. 1, a small, disc-shaped golf ball marker 30, formed of a ferrous material such as steel or soft iron, can be placed atop the fabric layer 22 and will be held secured in place on the upper, exterior surface of the fabric layer 22 until purposefully removed by a force that overcomes the force of magnetic attraction of the magnetic sheet 24. The ball marker 30 will be held in position regardless of the orientation of the hat 10. That is, the hat 10 may be removed from the head of the wearer, turned upside down, and otherwise manipulated without dislodging the ball marker 30 from the exposed surface of the fabric layer 22.

As is evident in FIG. 2, the use of a magnetic material permanently secured within the confines of a fabric covered article of golf clothing, allows the ball marker to be carried in such a way as to be immediately accessible for use and in a manner prominently displayed for all to view. Furthermore, other articles which are subject to magnetic attraction may be likewise releasably secured to the bill 16 of the cap 10. For example, and as illustrated in FIG. 1, an iron or steel golf divot repair tool 32 may also be placed in contact with the exposed surface of the fabric layer 22 and will remain secured to the bill 16 of the hat 10 until purposefully removed therefrom.

Figure 3:
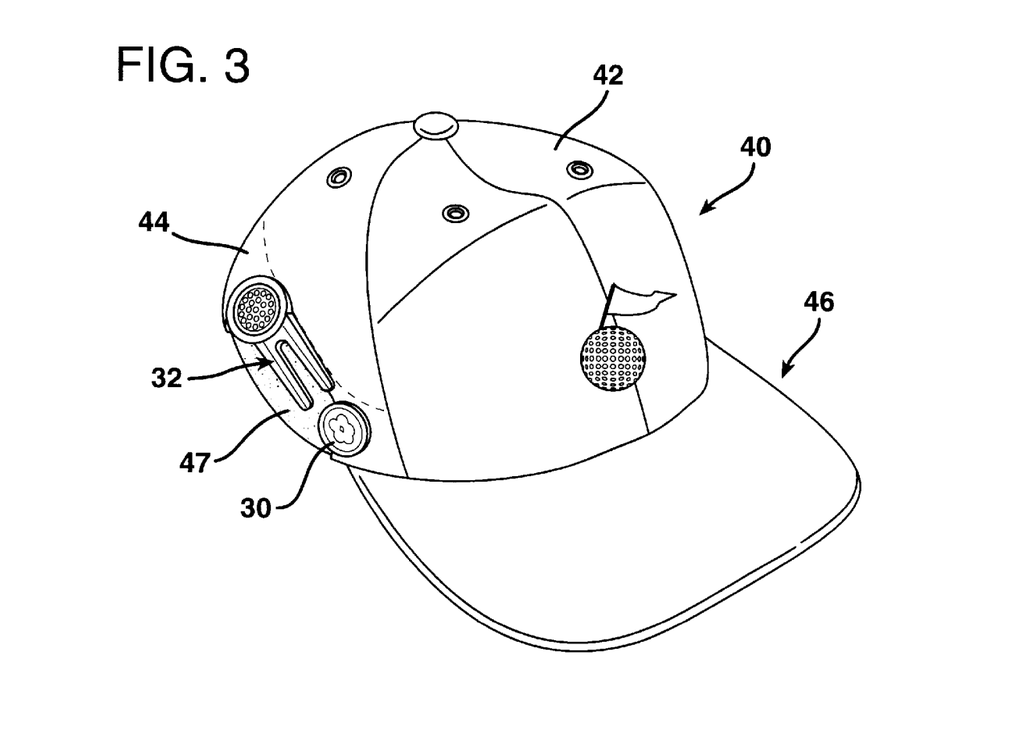
FIG. 3 is a perspective view, partially broken away, illustrating a golf cap or hat in which a strip of magnetic material has been secured in the hat band.

FIG. 3 illustrates an alternative construction of a golf hat 40. Like the golf hat 10, the hat 40 has a crown 42, a band 44 at the base of the crown 42, and a hat bill 46 projecting forwardly from the band region 44. However, the construction of the hat 40 differs from that of the hat 10 in that the bill 46 does not contain any magnetic material. Rather, an elongated strip 47 of magnetic material, such a strip 47 of flexible rubber in which magnetized ferrous particles of iron or iron oxide are embedded, is mounted within the hat band region 44 directly beneath the exposed fabric surface of the band region 44. A portion of the fabric covering the hat band region 44 is broken away in the illustration of FIG. 3 to reveal a portion of the magnetic strip 47 mounted therebeneath.

The strip 47 of magnetic material, like the sheet of magnetic material 24, exerts a force of magnetic attraction through the fabric covering at the band region 44. A golf ball marker 30 and also a golf divot tool 32 may thereby be placed in contact with the exposed fabric on the outside of the band region 44 of the hat 40, and will cling thereto due to the force of magnetic attraction of the strip 47 of magnetic material acting through the fabric of the hat 40. Other small, articles constructed wholly or partially of a ferrous material may also be carried on the fabric golf accessory of the invention. For example, a short pencil having a ferrous metal band will be held by the force of magnetic attraction if placed against either the band 44 of the hat 40 or against the bill 16 of the hat 10. Short pencils of this type are widely utilized by golfers for writing scores on core cards.

Figure 4:
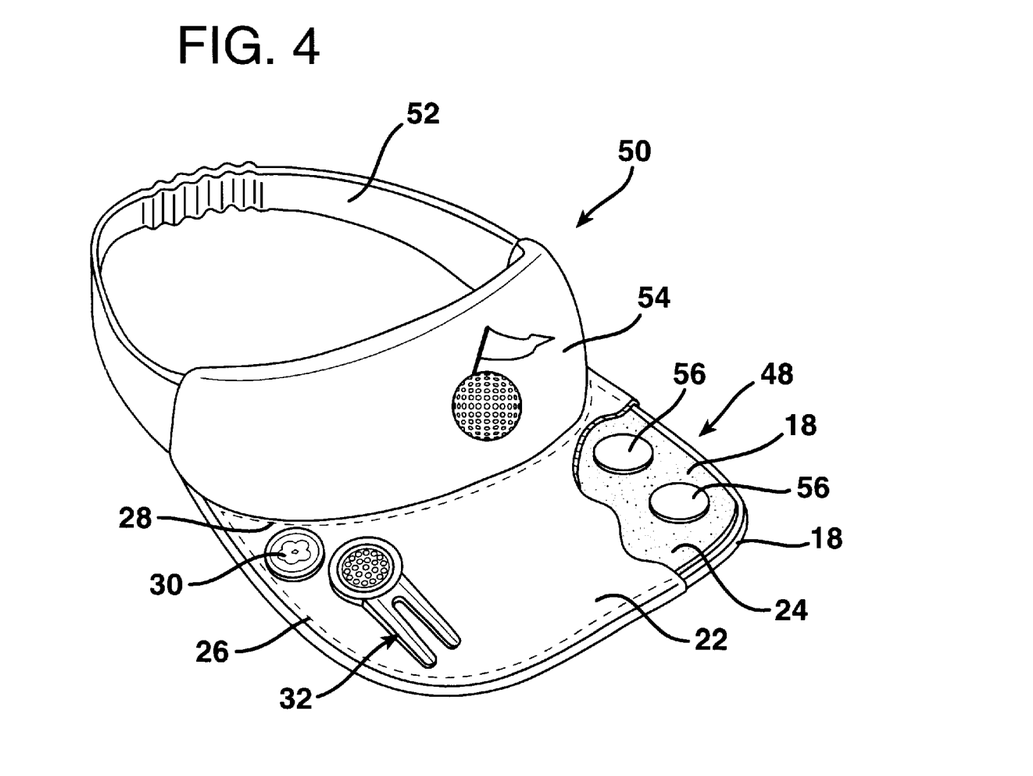
FIG. 4 is a perspective view which illustrates a golf sun visor having a fabric covered bill that encapsulates a plurality of flat magnets.

FIG. 4 illustrates still another article of golf clothing, namely a visor 50. The visor 50 does not have a crown, but rather is formed with an encircling fabric band 52, an enlarged forehead shield 54, and a bill 48 having a construction somewhat different from the bill 16 employed in the hat 10. Like the hat bill 16, the visor bill 48 is formed with a generally crescent-shaped stiffening core 18 wrapped with a sheet of fabric forming layers below and above the core, including an upper layer 22. However, the magnetic material interposed between the core 18 and the upper fabric layer is formed by a plurality of disc-shaped magnetic iron wafers 56, disposed atop the stiffening core 18 at intervals located near the edges of the bill 48. Each of the magnetic wafers 56 is about three-quarters of an inch in diameter and no greater than about one-eighth of an inch in thickness. Suitable magnetic wafers 56 may be obtained as Platform brand magnets from Arnold Engineering, located in Chicago, Ill. The magnetic wafers 56 may be secured by glue at desired locations atop the stiffening core 18. Lines of stitching 26 and 28 through the fabric forming the upper layer 22 and the lower fabric layer 20 anchor the fabric covering and secure the bill 48 to the forehead shield 54 of the visor 50. The force of magnetic attraction exerted by the magnetic material of the magnetic wafers 56 acts through the top fabric layer 22 and serves to attract and immobilize a ferrous ball marker 30, a ferrous divot tool 32, and any other small ferrous articles desired in position on the bill 48 of the visor 50 in a manner very similar to that depicted and described in conjunction with the golf hat 10 shown in Fig. 1.

Figure 5:
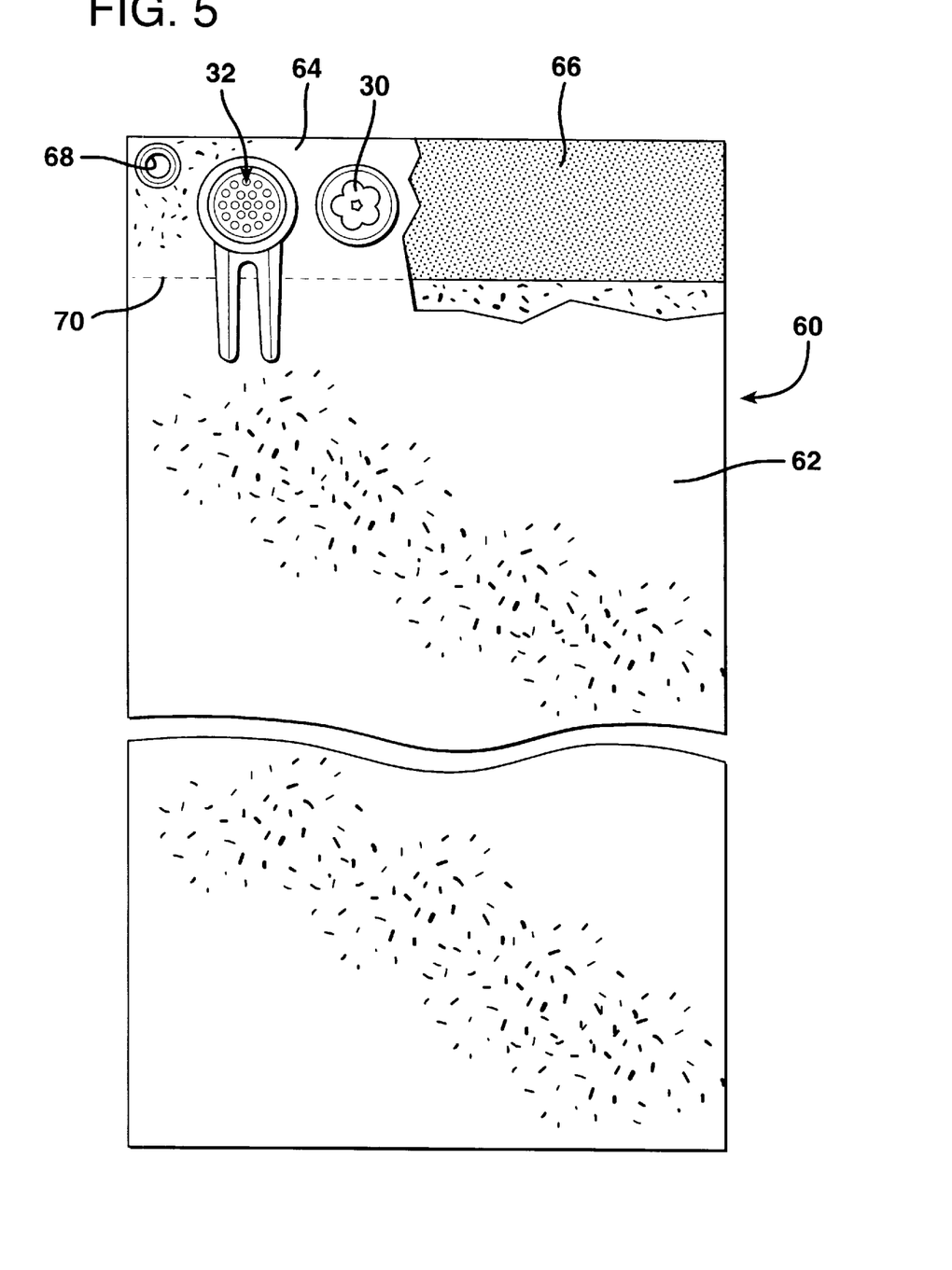
FIG. 5 illustrates a golf towel in which a strip of magnetic material has been sewn in a marginal seam.

FIG. 5 illustrates a combination in which the golf accessory involved is a golf towel 60. The golf towel 60 is formed of a sheet of terry cloth or linen 62 which is folded over at its top to form a two-ply upper marginal seam 64. Between the layers of fabric 62 there is a strip of magnetic material 66, which may be a narrow, flat strip of rubber with magnetized ferrous particles of iron or iron oxide imbedded therein. As with conventional golf towels, an annular metal grommet 68 is formed in a corner of the towel to allow the towel to be easily hung by a hook. Also, a transverse line of stitching 70 is sewn through the structure of the towel 60 about an inch from the upper edge of the towel. The grommet 68 passes through an opening in the magnetic strip 66 to prevent any transverse movement of the magnetic strip 66 relative to the towel 60. The magnetic strip 66 is thereby securely entrapped in position within the fabric structure of the towel 60.

As with the hats 10 and 40, the magnetic strip 66 exerts a significant magnetic field of attraction through both of the layers of the cloth 62 forming the towel 60. As a consequence, when an iron or steel ball marker 30 is placed in contact with the exposed surface of the fabric 62 adjacent the magnetic strip 66 lying therebeneath, the ball marker 30 will be held firmly in position and will not fall from the towel 60 despite use of the towel 60 for its intended purpose. Nevertheless, the ball marker 30 may be purposefully dislodged from the towel 60 by the golfer using a thumb and forefinger to lift the ball marker 30 away from the fabric 62 and out of the magnetic field created by the magnetic strip 66 in order to utilize the ball marker 30 to spot the location of a golf ball on a fairway or green. Similarly, an iron or steel divot tool 32 may likewise be removably attached to the golf towel 60.

Figure 6:
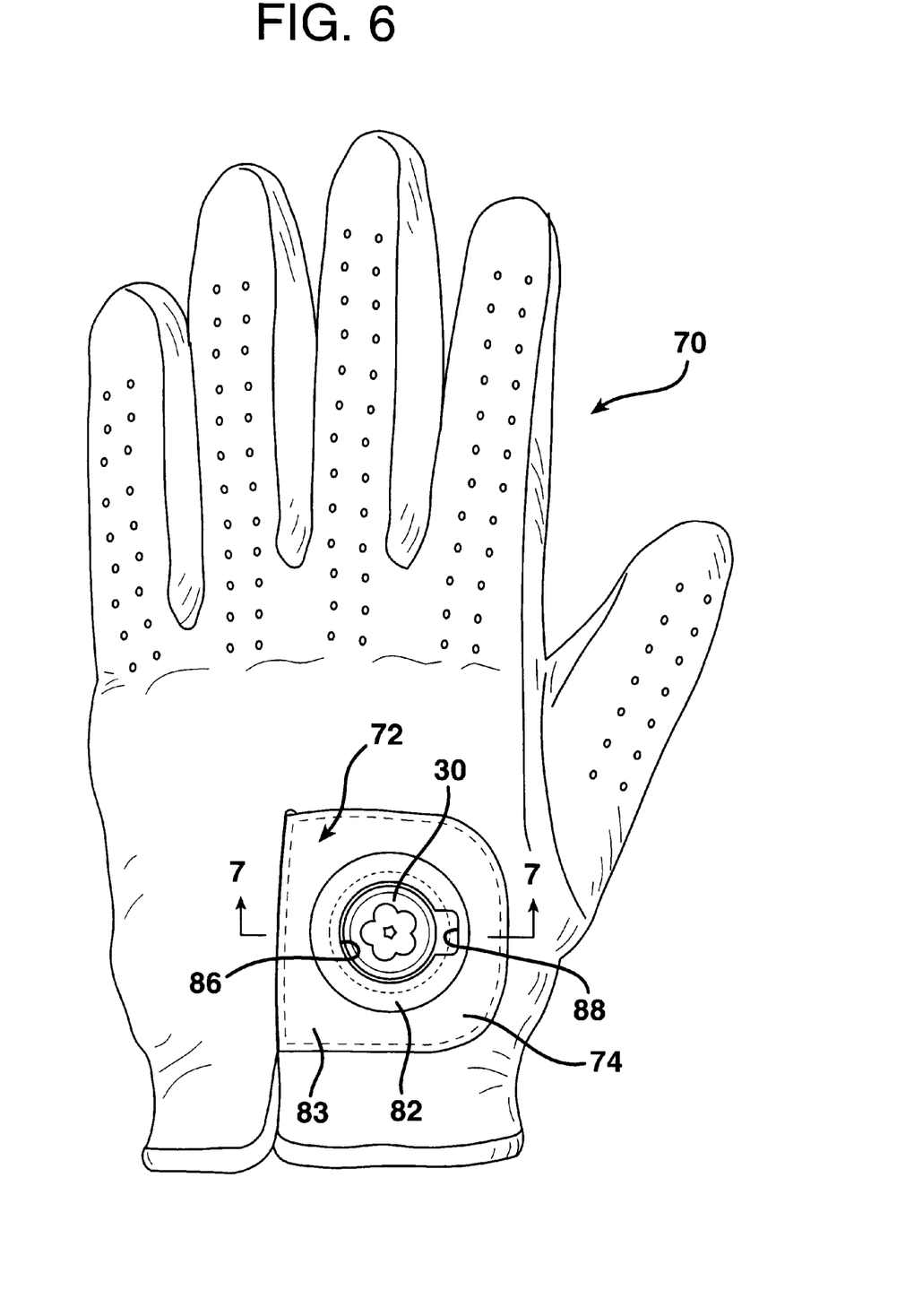
FIG. 6 illustrates a golf glove having a closure flap across the back in which a pad of magnetic material has been encapsulated to hold a golf ball marker in position thereatop.
Figure 7:
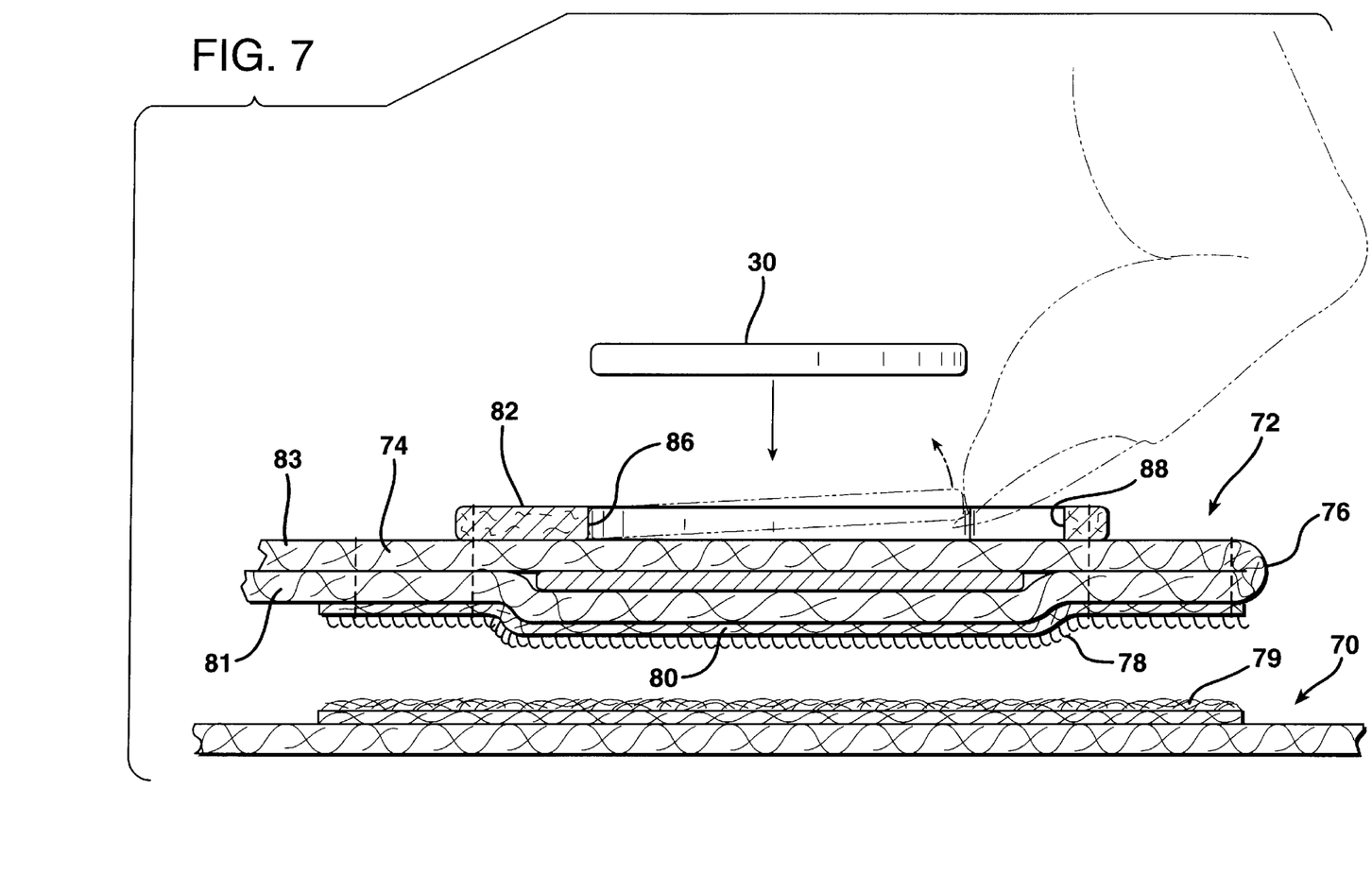
FIG. 7 is a section elevational detail taken along the lines 7—7 of FIG. 6.

FIGS. 6 and 7 illustrate another embodiment of the invention applied to a golfing glove 70. The golfing glove 70 is of the type often worn by golfers to ensure a firm grip on a club handle, particularly the handle of a driver. Like conventional golfing gloves, the glove 70 has fingers, a thumb, and an attachment flap 72 that passes across the back of the golfer's hand proximate the wrist area. As with conventional golf gloves, the flap 72 may incorporate a flexible, resilient, hook and look fabric fastener system employing a pad bearing a multiplicity of minute hooks 78 on the underside of the detached edge of the flap 72 that releasably engages a corresponding looped pile 79 of a pad sewn onto the outer surface of the back of the glove 70. Such conventional fabric hook and loop fastener systems are widely sold under the registered trademark Velcro®.

The fabric flap 72 may be formed of a leather strap 74 that extends from the body of the structure encasing the palm of the golfer's hand proximate the center thereof laterally across the back of the golfer's hand toward the base of the thumb. The flap 72 terminates in a free extremity 76 at which the end of the leather strap 74 is folded back underneath itself to form a double ply. A male pad of hook and loop fastener material from which a multiplicity of minute flexible fabric hooks 78 project is fastened by stitching on the lower layer 81 of the leather strap 74. The hooks 78 engage with a corresponding looped pile 79 facing outwardly from the body of the glove 70 beneath the flap 72. This fabric hook and loop wrist closure system is conventional, and need not be described in great detail.

Of greater significance, insofar as the present invention is concerned, is the presence of a generally flat, circular wafer 80 of rubberized magnetic material that is located in between the two plies 81 and 83 of the leather strap 74. The magnetic wafer 80 exerts a magnetic force that acts outwardly through the structure of the overlying upper layer 83 of the leather strap 74.

A generally annular-shaped patch of leather 82 is sewn to the flap 72 atop the upper layer 83 of the leather strap 74. The leather patch 82 has an outer perimeter that is circular in shape and also has central opening 86 defined therethrough. The central opening 86 in the leather patch 82 is also circular in shape throughout the greater portion of its perimeter but has a thumb recess 88. The thumb recess 88 in the central opening 86 in the leather patch 82 extends radially outwardly from the circular portion of the central opening 86. Since the leather patch 82 is sewn to the strap 74 near both its radial inner and outer peripheries, the central opening 86, together with the outer layer 83 of the strap 74 disposed immediately therebeneath, form a shallow, generally disc-shaped tray of a configuration suitable for receiving a ball marker 30 therewithin. The leather patch 82 thereby forms a flat retaining ring on the outer surface of the strap 72.

The retaining ring formed by the patch 82 is large enough to receive a golf ball marker 30 therewithin and thereby forms a seat that laterally surrounds the ball marker 30 atop the fabric surface of the upper leather layer 83 of the strap 74. The thumb recess 88 in the leather retaining ring provides a radial gap about one-quarter of an inch wide that allows the golfer to insert a fingernail into the recess 88 and beneath the ball marker 30 in order to lift the ball marker 30 free of the magnetic field exerted by the magnetic wafer 80. The radial recess 88 thereby facilitates removal of the ball marker 30 from within the seat defined by the central opening 86 and the exposed surface of the outer layer 83 of the leather strap 74.

Undoubtedly, numerous variations and modifications of the invention will become readily apparent to those familiar with golf accessories and the game of golf. For example, lengths of magnetized wire can be substituted for the flexible rubber sheet in which magnetized iron or iron oxide particles are embedded or the hard, magnetized wafers. Also, the use of the magnets is not limited to the particular articles of golf clothing or golf accessories depicted and described. For example, a magnet could be sewn into the seam of a shirt pocket or incorporated into a protruding end of a tongue of a golf shoe. Other variations of the invention are also possible. Therefore, the scope of the invention should not be construed as limited to the specific embodiments of the invention illustrated or the implementations of the method described.

I claim:

1. In combination, an article of golf clothing formed of a flexible material having an exterior surface, a magnetic material permanently attached to said article of clothing beneath said exterior surface thereof, whereby said magnetic material exerts a magnetic field of attraction that acts through said flexible material, and a golf ball marker formed of a ferrous material placed in contact with said exterior surface of said flexible material within said magnetic field, whereby said golf ball marker adheres to said article of clothing on said exterior surface thereof unless dislodged therefrom by a force stronger than said magnetic field.

2. A combination according to claim 1 wherein said article of golf clothing is a hat.

3. A combination according to claim 1 wherein said article of clothing is a sun visor.

4. A combination according to claim 1 wherein said article of clothing is a golfing glove.

5. In combination, a golf accessory constructed of fabric, a magnetic material permanently secured within the confines of said fabric so as to exert a force of magnetic attraction therethrough, and a golf ball marker formed of ferrous material located upon the exterior of said fabric within the field of said force of magnetic attraction, whereby said ball marker remains secured in place on said exterior of said fabric until removed by a force that overcomes said force of magnetic attraction.

6. A combination according to claim 5 wherein said golf accessory is formed as an article of headwear.

7. A combination according to claim 5 wherein said golf accessory is formed as a golfing glove.

8. A combination according to claim 5 wherein said golf accessory is formed as a golf towel.

9. A method of carrying a golf ball marker in open display on a fabric golf accessory comprising: securing a layer of magnetic material to a concealed surface of a layer of fabric of said golf accessory, and placing a golf ball marker formed of a ferrous material in contact with an exposed surface of said layer of fabric opposite said layer of magnetic material, whereby a magnetic field produced by said layer of magnetic material acts through said layer of fabric to hold said golf ball marker against said exposed surface of said layer of fabric until an opposing force stronger than said magnetic field dislodges said golf ball marker from said layer of fabric.

10. An improvement to a fabric golf visor having a stiff bill and a band attached to said bill for encircling the head of a wearer comprising a layer of magnetic material embedded in said bill, whereby the magnetic force of attraction of said magnetic material acts through the fabric structure of said visor.

* * * * *

EX PARTE REEXAMINATION CERTIFICATE (4891st)

United States Patent
Tate (10) Number: US 5,996,116 C1
(45) Certificate Issued: Jan. 6, 2004

(54) BALL MARKER RETENTION SYSTEM

(75) Inventor: John R. Tate, 11621 Markon Dr., Garden Grove, CA (US) 92841

(73) Assignee: John R. Tate, Garden Grove, CA (US)

Reexamination Request:
No. 90/005,832, Oct. 31, 2000

Reexamination Certificate for:
Patent No.: 5,996,116
Issued: Dec. 7, 1999
Appl. No.: 09/187,684
Filed: Nov. 5, 1998

(51) Int. Cl.[7] .................................................. A42B 1/24
(52) U.S. Cl. .............................. 2/12; 2/195.1; 2/200.1; 2/209.13; 2/425; 224/918
(58) Field of Search .......................... 2/209.13, 175.1, 2/195.1, 160, 161.1, 161.2, 161.5, 161.4, 12; 351/155; 428/361, 900

(56) References Cited

U.S. PATENT DOCUMENTS

| | | |
|---|---|---|
| 459,942 A | 9/1891 | Brown |
| 2,597,601 A | 4/1952 | Sherman |
| 2,693,654 A | 11/1954 | Clark |
| 3,136,547 A | 6/1964 | Schaper |
| 3,208,123 A | 9/1965 | Koos |
| 3,233,802 A | 2/1966 | Ludwick |
| 3,321,119 A | 5/1967 | D'Andrea |
| 3,546,709 A | 12/1970 | Cross |
| 3,895,797 A * | 7/1975 | Moore ........................ 273/32 |
| 4,130,950 A | 12/1978 | Bazzle et al. |
| 4,489,444 A | 12/1984 | Graham |
| 4,627,621 A | 12/1986 | Tate |
| 4,826,059 A | 5/1989 | Bosch et al. |
| 4,885,195 A | 12/1989 | Change, III |
| 5,135,220 | 8/1992 | Baldoni |
| 5,295,683 | 3/1994 | Tate |
| 5,305,999 | 4/1994 | Tate |
| 5,364,094 | 11/1994 | Mustion |
| 5,544,361 * | 8/1996 | Fine et al. ........................ 2/10 |
| 5,593,073 | 1/1997 | Finnegan |
| 5,715,539 | 2/1998 | Benecki et al. |
| 5,898,943 | 5/1999 | Kim |
| 5,898,946 | 5/1999 | Keating et al. |
| 5,950,239 * | 9/1999 | Lopez ........................ 2/115 |
| 6,052,828 * | 4/2000 | Widdemer ................ 2/161.2 |
| 6,174,058 * | 1/2001 | Hsiao ........................ 351/155 |
| 6,175,963 * | 1/2001 | Loeffelholz ............... 2/204.13 |

FOREIGN PATENT DOCUMENTS

| | | |
|---|---|---|
| CA | 2126169 | 12/1994 |
| CA | 2219612 | 10/1997 |

OTHER PUBLICATIONS

Make Your Mark Golf Accessories, Inc. advertising brochure.

* cited by examiner

*Primary Examiner*—K Moran (57) ABSTRACT

A golf ball marker is carried in open display on a fabric article of golf clothing or other fabric golf accessory and remains in position due to the force of magnetism. To produce this effect, a layer of magnetic material is secured in position in contact with a concealed side of a layer of fabric in the article of golf clothing or other golf accessory. The golf ball marker is constructed of a ferrous material so that when it is placed into contact with an exposed surface of the same layer of fabric against which the magnetic material is secured opposite the layer of magnetic material, the ball marker is held by the force of magnetic attraction against the exposed surface of the to fabric layer. The ball marker remains in position until purposefully dislodged by a force that opposes the magnetic field created by the magnetic material. This force may be applied by the thumb and forefinger of the golfer's hand to remove the golf ball marker from the fabric layer. The layer of magnetic material may be incorporated into the bill or band of a hat or cap, the bill or band of a golf sun visor, the closure flap of a golfing glove, or in a golf towel.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4, 7, 8 and 10 is confirmed.

Claims 1–3, 5, 6 and 9 are cancelled.

New claims 11–33 are added and determined to be patentable.

*11. In combination, an article of golf clothing formed of a flexible material having an exterior surface and a stiff core concealed beneath said flexible material, a magnetic material permanently attached to said article of clothing beneath said exterior surface of said flexible fabric material and secured in position with respect to said core and in direct contact with said flexible material, whereby said magnetic material exerts a magnetic field of attraction that acts through said flexible material, and a golf ball marker formed of a ferrous material placed in contact with said exterior surface of said flexible material within said magnetic field, whereby said golf ball marker adheres to said article of clothing on said exterior surface thereof unless dislodged therefrom by a force stronger than said magnetic field.*

*12. A combination according to claim 11 wherein said magnetic material has at least one flat surface and said magnetic element is secured to said core so that the entire area of said flat surface is held in direct contact with said flexible material.*

*13. In combination, a golf accessory constructed of fabric and a stiff core concealed beneath said fabric, a magnetic material permanently secured relative to said stiff core and within the confines of said fabric so as to exert a force of magnetic attraction therethrough, and a golf ball marker formed of ferrous material located upon the exterior of said fabric within the field of said force of magnetic attraction, whereby said ball marker remains secured in place on said exterior of said fabric until removed by a force that overcomes said force of magnetic attraction.*

*14. A combination according to claim 13 wherein said magnetic material has at least one flat surface and is held in contact with said stiff core structure and said fabric is held in direct contact with said flat surface of said magnetic material.*

*15. A method of carrying a golf ball marker in open display on a fabric golf accessory comprising: securing one side of a layer of magnetic material against a concealed surface of a layer of fabric of said golf accessory while supporting said layer of magnetic material by a stiff core concealed by said layer of fabric, and placing a golf ball marker formed of a ferrous material in contact with an exposed surface of said layer of fabric opposite said layer of magnetic material, whereby a magnetic field produced by said layer of magnetic material acts through said layer of fabric to hold said golf ball marker against said exposed surface of said layer of fabric until an opposing force stronger than said magnetic field dislodges said golf ball marker from said layer of fabric.*

*16. In combination, an article of golf headwear formed with a bill and a flexible material having an exterior surface, a magnetic material permanently attached to said bill of said article of headwear beneath said exterior surface of said flexible material, whereby said magnetic material exerts a magnetic field of attraction that acts through said flexible material, and a golf ball marker formed of a ferrous material placed on said bill in contact with said exterior surface of said flexible material within said magnetic field, whereby said golf ball marker adheres to said bill of said article of golf headwear on said exterior surface thereof unless dislodged therefrom by a force stronger than said magnetic field.*

*17. A combination according to claim 16 wherein said article of golf headwear is a hat.*

*18. A combination according to claim 16 wherein said article of headwear is a sun visor.*

*19. A combination according to claim 16 wherein said bill has a flat, stiff interior core and said magnetic material is secured relative to and in direct contact with said core of said bill.*

*20. In combination, an article of golf headwear constructed with a bill having a stiff core and fabric overlying said core, a magnetic material permanently secured relative to and in direct contact with said core of said bill and within the confines of said fabric so as to exert a force of magnetic attraction therethrough, and a golf ball marker formed of ferrous material located upon the exterior of said fabric within the field of said force of magnetic attraction, whereby said ball marker remains secured in place on said exterior of said fabric on said bill until removed by a force that overcomes said force of magnetic attraction.*

*21. A method of carrying a golf ball marker in open display on an article of golf headwear having a bill with a stiff core comprising: securing a layer of magnetic material relative to and in direct contact with said core of said bill beneath a concealed surface of a layer of fabric of said article of golf headwear, and placing a golf ball marker formed of a ferrous material in contact with an exposed surface of said layer of fabric on said bill opposite said layer of magnetic material, whereby a magnetic field produced by said layer of magnetic material acts through said layer of fabric to hold said golf ball marker against said bill and on said exposed surface of said layer of fabric until an opposing force stronger than said magnetic field dislodges said golf ball marker from said layer of fabric.*

*22. A combination according to claim 11 wherein said magnetic material is comprised of a magnetic iron wafer.*

*23. A combination according to claim 22 wherein said magnetic iron wafer is disk-shaped and is no greater than about one-eighth of an inch in thickness.*

*24. A combination according to claim 13 wherein said magnetic material is comprised of a magnetic iron wafer.*

*25. A combination according to claim 24 wherein said magnetic iron wafer is disk-shaped and is no greater than about one-eighth of an inch in thickness.*

*26. A combination according to claim 15 wherein said magnetic material is comprised of a magnetic iron wafer.*

*27. A combination according to claim 26 wherein said magnetic iron wafer is disk-shaped and is no greater than about one-eighth of an inch in thickness.*

*28. A combination according to claim 16 wherein said magnetic material is comprised of a magnetic iron wafer.*

29. A combination according to claim 28 wherein said magnetic iron wafer is disk-shaped and is no greater than about one-eighth of an inch in thickness.

30. A combination according to claim 20 wherein said magnetic material is comprised of a magnetic iron wafer.

31. A combination according to claim 30 wherein said magnetic iron wafer is disk-shaped and is no greater than about one-eighth of an inch in thickness.

32. A combination according to claim 21 wherein said magnetic material is comprised of a magnetic iron wafer.

33. A combination according to claim 32 wherein said magnetic iron wafer is disk-shaped and is no greater than about one-eighth of an inch in thickness.

* * * * *